(12) United States Patent
Liu (10) Patent No.: US 10,610,108 B2
(45) Date of Patent: Apr. 7, 2020

(54) PORTABLE DEVICE AND PORTABLE DEVICE ASSEMBLY

(71) Applicant: BOE TECHNOLOGY GROUP CO., LTD., Beijing (CN)

(72) Inventor: Kairan Liu, Beijing (CN)

(73) Assignee: BOE TECHNOLOGY GROUP CO., LTD., Beijing (CN)

(*) Notice: Subject to any disclaimer, the term of this patent is extended or adjusted under 35 U.S.C. 154(b) by 0 days.

(21) Appl. No.: 15/572,074

(22) PCT Filed: May 12, 2017

(86) PCT No.: PCT/CN2017/084091
§ 371 (c)(1),
(2) Date: Nov. 6, 2017

(87) PCT Pub. No.: WO2017/198113
PCT Pub. Date: Nov. 23, 2017

(65) Prior Publication Data
US 2019/0110693 A1    Apr. 18, 2019

(30) Foreign Application Priority Data
May 16, 2016 (CN) .......................... 2016 1 0323243

(51) Int. Cl.
*A61B 5/01* (2006.01)
*A61B 5/053* (2006.01)
(Continued)

(52) U.S. Cl.
CPC .............. *A61B 5/01* (2013.01); *A61B 5/0077* (2013.01); *A61B 5/053* (2013.01); *A61B 5/0531* (2013.01);
(Continued)

(58) Field of Classification Search
CPC ........... A61B 5/01; A61B 5/00; A61B 5/0077; A61B 5/053; A61B 5/0531;
(Continued)

(56) References Cited

U.S. PATENT DOCUMENTS

| 2011/0077497 A1 | 3/2011 | Oster et al. |
| 2015/0265214 A1 | 9/2015 | De Kok et al. |
| 2017/0031334 A1 | 2/2017 | Medelius |

FOREIGN PATENT DOCUMENTS

| CN | 102065751 A | 5/2011 |
| CN | 104224115 A | 12/2014 |

(Continued)

OTHER PUBLICATIONS

International Search Report and Written Opinion for Application No. PCT/CN2017/084091, dated Jul. 27, 2017, 10 Pages.

*Primary Examiner* — Paula J Stice
(74) *Attorney, Agent, or Firm* — Brooks Kushman P.C.

(57) ABSTRACT

A portable device is provided, including a wearable frame capable of switching at least between a first status and a second status for a user to wear on different body parts. In the first status, the wearable frame forms a wristband for the user to wear, and in the second status, the wearable frame forms a hair clip for the user to wear on head. The wearable frame is provided with a physiological status information collection unit, used to collect physiological status information of a skin or hair of the user; and an environment information collection unit, used to collect external environment information of an environment where the user is located; and a communication unit, used to send the physiological status information and the external environment information to an external terminal. A portable device assembly is also provided.

17 Claims, 5 Drawing Sheets

(51) Int. Cl.
*A61B 5/00* (2006.01)
*A61B 5/145* (2006.01)

(52) U.S. Cl.
CPC .......... *A61B 5/14539* (2013.01); *A61B 5/443* (2013.01); *A61B 5/448* (2013.01); *A61B 5/6814* (2013.01); *A61B 5/6824* (2013.01); *A61B 2560/0242* (2013.01)

(58) Field of Classification Search
CPC ..... A61B 5/14539; A61B 5/443; A61B 5/448; A61B 5/6814; A61B 5/6824; A61B 2560/0242
See application file for complete search history.

(56) References Cited

FOREIGN PATENT DOCUMENTS

| | | |
|---|---|---|
| CN | 204500717 U | 7/2015 |
| CN | 105286839 A | 2/2016 |
| CN | 205107662 U | 3/2016 |
| CN | 106037637 A | 10/2016 |
| CN | 205697717 U | 11/2016 |
| WO | 2015157670 A1 | 10/2015 |

PORTABLE DEVICE AND PORTABLE DEVICE ASSEMBLY

CROSS-REFERENCE TO RELATED APPLICATIONS

This application is the U.S. national phase of PCT Application No. PCT/CN2017/084091 filed on May 12, 2017, which claims priority to Chinese Patent Application No. 201610323243.8 filed on May 16, 2016, which are incorporated herein by reference in their entireties.

TECHNICAL FIELD

The present disclosure relates to an intelligent product, and more particularly, to a portable device and a portable device assembly.

BACKGROUND

At present, some intelligent wearable products with ultraviolet (UV) detection function can provide users with reminders or suggestions, to protect users against suntan or sunburn in outdoor activities. Different persons have different skin conditions, the skin condition of one person may change now and then within a day, so the user may input his skin condition inaccurately during initial setting based on his self judgment on his skin condition. Not only the skin will be damaged by UV, the hair is also apt to lose toughness after exposure to the sun and may become dry and yellow. If the hair is exposed to the sun for a long time, proteins in the hair may be decomposed by UV, such that the hair may lose elasticity and luster. Therefore, it is required that the intelligent wearable product can provide effective and comprehensive UV detection function for individual users.

SUMMARY

The embodiments of the present disclosure provide a portable device and a portable device assembly, which can detect external environment information and individual physiological status information of each user, and can provide the user with more accurate and comprehensive suggestions.

It is provided a portable device in some embodiments of the present disclosure, and the portable device includes: a wearable frame which is capable of switching at least between a first status and a second status, where the wearable frame has different shapes in the first status and the second status. The wearable frame is provided with: a physiological status information collection unit, used to collect physiological status information of a user; an environment information collection unit, used to collect external environment information of an environment where the user is located; and a communication unit, used to send the physiological status information and the external environment information to an external terminal.

Optionally, in the first status, the wearable frame is in a ring shape, and in the second status, the wearable frame is in a clip shape.

Optionally, the physiological status information collection unit includes a bioelectric impedance analysis (BIA) sensor. The BIA sensor is used to: obtain biological tissue status information of a skin of the user in the case that the wearable frame is in the first status; and obtain biological tissue status information of a hair of the user in the case that the wearable frame is in the second status.

Optionally, the physiological status information collection unit includes a first temperature sensor. The first temperature sensor is used to: obtain a temperature of the skin of the user in the case that the wearable frame is in the first status; and obtain a temperature of the hair of the user in the case that the wearable frame is in the second status.

Optionally, the physiological status information collection unit includes a Potential of Hydrogen (pH) sensor. The pH sensor is used to: obtain a pH value of the skin of the user in the case that the wearable frame is in the first status; and obtain a pH value of the hair of the user in the case that the wearable frame is in the second status.

Optionally, the physiological status information collection unit includes a camera having an enlarging function. The camera is used to: obtain the information of the skin of the user in an enlarging status in the case that the wearable frame is in the first status; and obtain the information of the hair of the user in an enlarging status in the case that the wearable frame is in the second status.

Optionally, the environment information collection unit includes at least one of the following: an ultraviolet sensor used to detect an ultraviolet intensity, an air quality sensor used to detect an air quality, a second temperature sensor used to detect a temperature of an external environment, and a humidity sensor used to detect a humidity of the external environment.

Optionally, the wearable frame includes a first part and a second part connected through a connector, the first part can turn over around the connector to make the wearable frame change between the first status and the second status, the physiological status information collection unit is arranged at the first part, and the environment information collection unit is arranged at the second part.

Optionally, both the first part and the second part are in a semi-arc structure, a first end of the first part is connected to a first end of the second part through the connector, and a second end of the first part and a second end of the second part are magnetically attached to each other through magnets.

Optionally, the connector includes a first rotating bead and a second rotating bead connected through a first shaft, the first rotating bead is connected to the first part through a second shaft, and the second rotating bead is connected to the second part through a third shaft.

Optionally, the first rotating bead is sleeved on the first shaft and can rotate around the first shaft, the second shaft and the third shaft are parallel and are both perpendicular to the first shaft, the first rotating bead is sleeved on the second shaft, and the second rotating bead is sleeved on the third shaft.

Optionally, the connector is an elastic structure having a third status and a fourth status, and the first part or the second part is provided with an accommodating space. In the case that the connector is in the third status, the connector is retracted inside the accommodating space to make the first part closely contact with the second part; and in the case that the connector is in the fourth status, the connector is in a stretching status and there is a gap between the first part and the second part.

Optionally, the wearable frame is coated by a shell made of an electro-chromic material, and the electro-chromic material can display different colors when driven by an electric field.

Optionally, the communication unit is further used to receive a health suggestion returned by the external terminal; and the portable device further includes: an informing unit which is arranged on the wearable frame and used to inform the user of the health suggestion returned by the external terminal.

Optionally, the information prompt unit includes: a loudspeaker, used to report the health suggestion to the user through a voice prompt, or a display screen, used to display the health suggestion to the user.

It is also provided a portable device assembly in some embodiments of the present disclosure, and the portable device assembly includes the portable device above, and further includes a mobile terminal. The communication unit of the portable device is used to send the physiological status information and the external environment information to the mobile terminal.

Further, the mobile terminal includes: an information processing unit, used to obtain a health suggestion suitable for the user according to the information sent by the communication unit; an informing unit, used to inform the user of the health suggestion. The informing unit may include: a loudspeaker, used to report the health suggestion to the user through a voice prompt, or a display screen, used to display the health suggestion to the user.

The portable device provided in the present disclosure can be set into a variety of forms to facilitate the application, and can detect the external environment information and the individual physiological status information of each user simultaneously, so as to combine external environment factors with the individual physiological status of the user to give appropriate suggestions to the user.

DETAILED DESCRIPTION

The principles and features the present disclosure will be described hereinafter in detail in conjunction with the drawings and specific embodiments. The embodiments in following description are intended to explain the present disclosure, rather than to limit the scope of protection of the present disclosure.

As shown in FIG. 1 to FIG. 9, it is provided a portable device according to some embodiments of the present disclosure, including: a wearable frame capable of switching at least between a first status and a second status, where the wearable frame has different shapes in the first status and the second status.

The wearable frame is provided with:
a physiological status information collection unit, used to collect physiological status information of a user;
an environment information collection unit, used to collect external environment information about an environment where the user is located; and
a communication unit, used to send the physiological status information and the external environment information to an external terminal.

Optionally, in the first status, the wearable frame is in a ring shape, and in the second status, the wearable frame is in a clip shape. For example, in the first status, the wearable frame forms a wristband for the user to wear, and in the second status, the wearable frame forms a hair clip for the user to wear on hair. In the embodiments of the present disclosure, the portable device can have a variety of forms including a ring shape, a clip shape, or the like, and can detect the physiological status information of the user and the external environment information in real time, so as to combine external environment factors with individual physiological status of the user to give appropriate suggestions to the user more accurately and comprehensively.

In order to give appropriate suggestions to the user more accurately and comprehensively, the specific structure of the physiological status information collection unit may have a variety of forms, and can collect physiological status information of various body parts of the user, where various body parts can be set according to actual requirements.

In some embodiments of the present disclosure, the physiological status information collection unit includes: a bioelectric impedance analysis (BIA) sensor 11 used to obtain biological tissue status information of skin or hair.

Regarding the detection on the physiological status of the user, intracellular and extracellular liquid impedances can be detected by configuring the BIA sensor, so as to obtain the biological tissue status information. Generally, a tiny alternating current or voltage signal is applied to a test object by means of a measuring electrode arranged on a body surface, and with respect to different application purposes, relational biological tissue status information can be obtained by detecting corresponding impedance and changing of the corresponding impedance. In the case that the user does not wear a hat, the wearable frame of the portable device can be set in the hair clip shape and clipped on the hair as a hair clip, and a corresponding mode is set into a hair clip mode; here, real-time moisture change of the hair can be obtained through the BIA sensor 11. In the case that the wearable frame of the portable device is set in a wristband shape, a corresponding mode is set into a wristband mode; here, condition of the skin such as water-oil balancing condition of the skin can be obtained through the BIA sensor 11. Furthermore, in order to detect condition of other parts such as face condition, the BIA sensor can be arranged in contact with skin of the face.

Optionally, the physiological status information collection unit includes: a first temperature sensor 12 used to obtain a temperature of the skin or hair.

In the case that the wearable frame is in the first status, the portable device can be worn on a hand of the user in the wristband shape; here, the temperature of the skin of the user can be detected by the first temperature sensor 12.

In the case that the wearable frame is in the second status, the portable device can be worn on the hair of the user in the hair clip shape; here, the temperature of the hair of the user can be detected by the first temperature sensor 12.

Optionally, the physiological status information collection unit includes: a potential of hydrogen (pH) sensor 13 used to obtain a pH value of the skin or hair.

A pH value of a neutral skin ranges from 5 to 5.6, a pH value of a dry skin ranges from 4.5 to 5, a pH value of an oily skin ranges from 5.6 to 6.6, and the hair is in a best health status when a pH value of the hair ranges from 4.5 to 5.5. By detecting the pH value, the user may better understand his condition and may determine whether the cosmetic and shampoo he uses currently are suitable for him.

Optionally, the physiological status information collection unit includes: a camera having an enlarging function, used to obtain information about the skin or the hair in an enlarging status.

By adding the camera having the enlarging function, the wearable frame when being in the second status can form a hair clip for the user to wear on the hair, and the user can turn on the camera to observe hair condition such as condition of the hair cuticle; and the wearable frame when being in the first status can form a wristband for the user to wear, and the user can observe the condition of his skin in the enlarging status through the camera during skin detection.

Optionally, the user may select whether the camera is to be turned on or not according to actual requirements, and the camera can be only turned on in the case that the user selects to turn on the camera.

It should be noted that it is described above exemplarily that the wearable frame has the wristband shape and the hair clip. In practical application, the wearable frame can be worn on any body part of the user in a ring shape to collect the physiological status information of the skin of the body part of the user, and can be changed from the ring shape to any clip shape to collect the physiological status information of the hair of the user. The ring shape is not limited to the wristband, and the clip shape is not limited to the hair clip.

Optionally, the environment information collection unit includes at least one of the following: an ultraviolet sensor 21 used to detect an ultraviolet intensity, an air quality sensor 22 used to detect an air quality, a second temperature sensor 23 used to detect a temperature of the external environment, and a humidity sensor 24 used to detect a humidity of the external environment.

It should be noted that the environment information collection unit may also include a sensor for detecting other environmental factor, which may be set according to actual requirements.

Optionally, the communication unit is further used to receive a health suggestion returned from the external terminal; and the portable device further includes: an informing unit which is arranged on the wearable frame and used to inform the user of the health suggestion returned from the external terminal.

Further, the informing unit includes: a loudspeaker, which is used to report the health suggestion to the user through a voice prompt, or a display screen, which is used to display the health suggestion to the user.

The portable device acquires data of the external environment and the individual physiological status of the user in real time through the physiological status information collection unit and the environment information collection unit, and then uploads the data to the external terminal (such as a cloud processor) for analysis and storage, and the communication unit receives an suggestion which is fed back by the external terminal to the user and is suitable for the environment in which the user is located. For instance, in the case of sun exposure, the user may be prompted whether to go to a cool place to prevent sunstroke or whether to apply some spray to his hair for protection based on combination of an ultraviolet amount received by the hair detected by the ultraviolet sensor, a temperature of the hair collected by the first temperature sensor 12, a moisture content of the hair collected by the BIA sensor 11, and the pH value of the hair collected by the pH sensor 13. Meanwhile, the longer the user uses the portable device, the more the user data stored in the cloud processor; in this way, a suggestion can be given to the user more quickly and accurately, and even a suggestion can be given in advance by predicting a user demand. The suggestion suitable for the user can be reported to the user through the loudspeaker or displayed to the user through the display screen.

Figure 1:
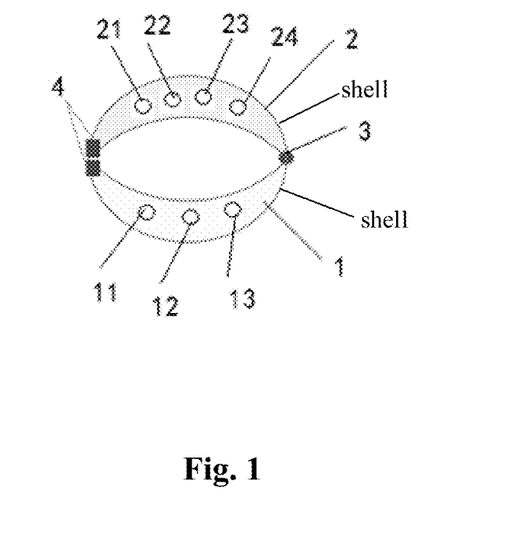
FIG. 1 shows a portable device in a wristband shape according to some embodiments of the present disclosure.
Figure 2:
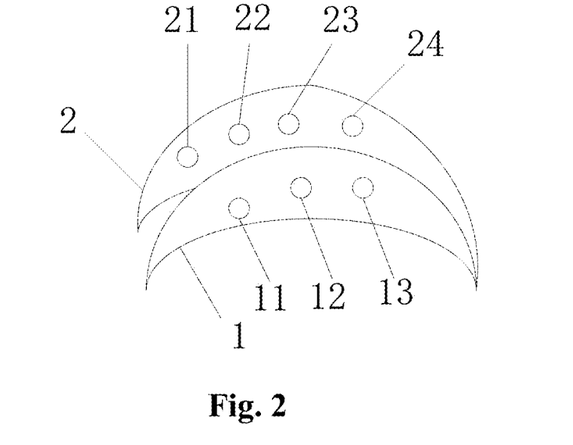
FIG. 2 shows a portable device in a hair clip shape according to some embodiments of the present disclosure.

In some embodiments, as shown in FIG. 1 and FIG. 2, the wearable frame includes a first part 1 and a second part 2 connected through a connector 3, the first part 1 can turn over around the connector 3 to make the wearable frame change between the first status and the second status, the physiological status information collection unit is arranged at the first part 1, and the environment information collection unit is arranged at the second part 2.

Optionally, both the first part 1 and the second part 2 are in a semi-arc structure, a first end of the first part 1 is connected to a first end of the second part 2 through the connector 3, and a second end of the first part 1 and a second end of the second part 2 are magnetically attached to each other through magnets 4.

Figure 4:
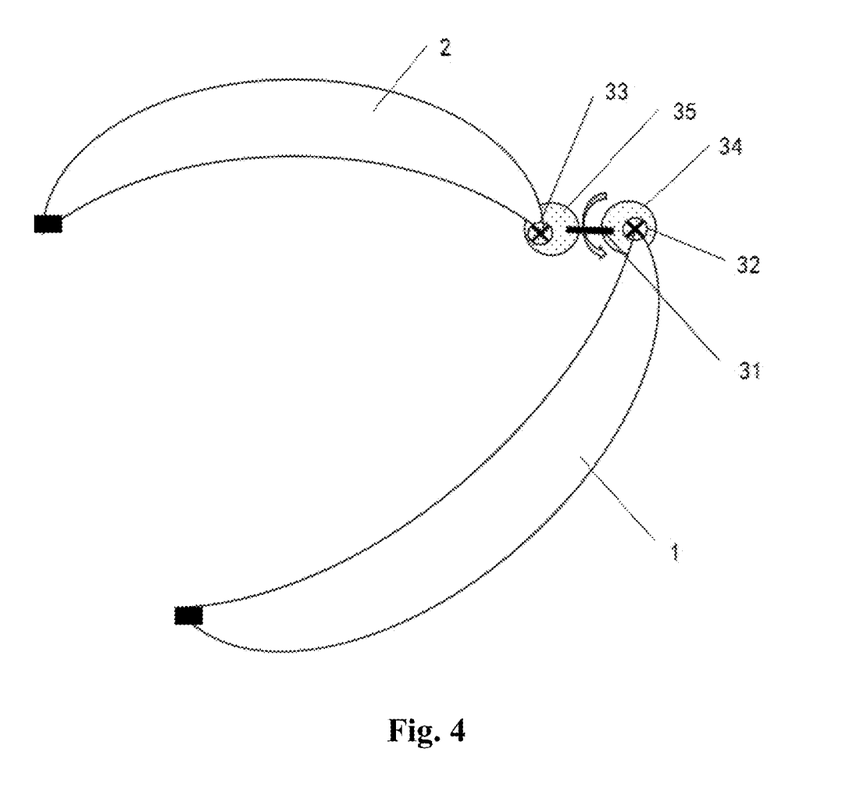
FIG. 4 shows a schematic structural diagram of a first part and a second part separated by a certain angle according to some embodiments of the present disclosure.
Figure 5:
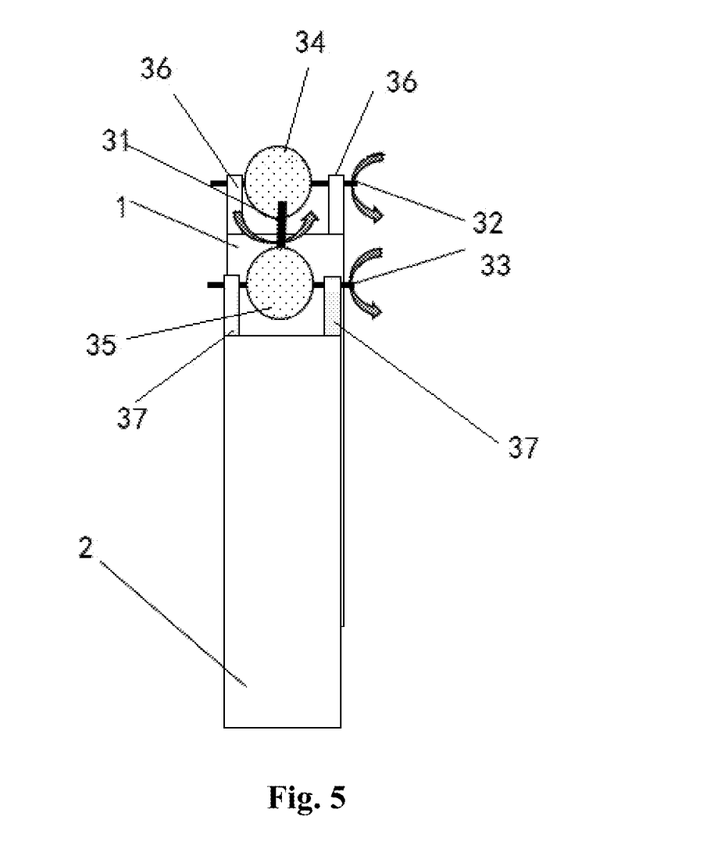
FIG. 5 shows a top view of the structure in FIG. 4.

Further, as shown in FIG. 4 and FIG. 5, the connector 3 includes a first rotating bead 34 and a second rotating bead 35 connected through a first shaft 31, the first rotating bead 34 is connected to the first part 1 through a second shaft 32, and the second rotating bead 35 is connected to the second part 2 through a third shaft 33, where directions of arrows in the figures represent rotating directions around corresponding shafts. The first rotating bead 34 is sleeved on the first shaft 31, and when the first part 1 turns over around the first shaft 31, the first rotating bead 34 rotates around the first shaft 31. In some embodiments of the present disclosure, the second part 2 can be turned over to switch the wearable frame between the wristband shape and the hair clip shape; here, the second rotating bead 35 can be sleeved on the first shaft 31 and can rotate around the first shaft 31.

As shown in FIG. 4, the first rotating bead 34 and the second rotating bead 35 are respectively connected to the first part 1 and the second part 2, and the first rotating bead 34 and the second rotating bead 35 are connected by the first shaft 31 which is horizontally arranged, so that the first part 1 can rotate around the first shaft 31 to turn over up and down relative to the second part 2, i.e., turn over to a position above the second part 2 from a position below the second part 2, and turn over to the position below of the second part 2 from of the position above the second part 2.

The first rotating bead 34 is connected to the first part 1 through the second shaft 32, the first end of the first part 1 extends towards a direction away from the second end of the first part to form two first connecting plates 36 that are arranged oppositely, through holes are provided at corresponding positions of the two first connecting plates 36 for the second shaft 32 to pass through, and the first rotating bead 34 is sleeved on the second shaft 32. As shown in FIG. 4, the second shaft 32 is arranged perpendicular to the paper, and the first part 1 can rotate around the second shaft 32 in a plane of the paper. The second rotating bead 35 is connected to the second part 2 through the third shaft 33, the first end of the second part 2 extends towards a direction away from the second end of the second part to form two second connecting plates 37 that are arranged oppositely, through holes are provided at corresponding positions of the two second connecting plates 37 for the third shaft 33 to pass through, and the second rotating bead 35 is sleeved on the third shaft 33. As shown in FIG. 4, the third shaft 33 is arranged perpendicular to the paper, and the second part 2 can rotate around the third shaft 33 in a plane of the paper. In the case that the wearable frame is used in the wristband shape, by rotating the first part 1 around the second shaft 32 and/or rotating the second part 2 around the third shaft 33, the wristband can be opened and a size of an opening of the wristband, i.e., an opening angle between the first part 1 and the second part 2 can be adjusted.

In the case that the wearable frame is in the first status, the first part 1 and the second part 2 each having a semi-arc structure are arranged oppositely to form a wristband, as shown in FIG. 1.

Figure 3:
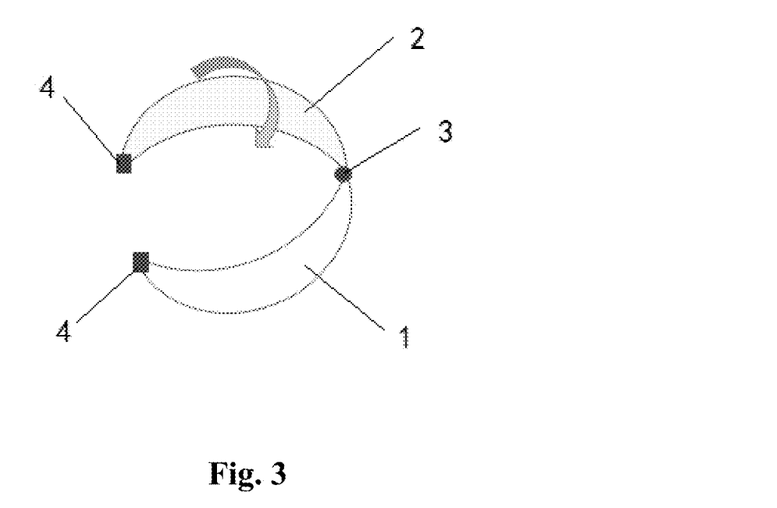
FIG. 3 shows a schematic view of a portable device changed from a wristband shape to a state that a second end of a first part is separated from a second end of a second part according to some embodiments of the present disclosure.
Figure 6:
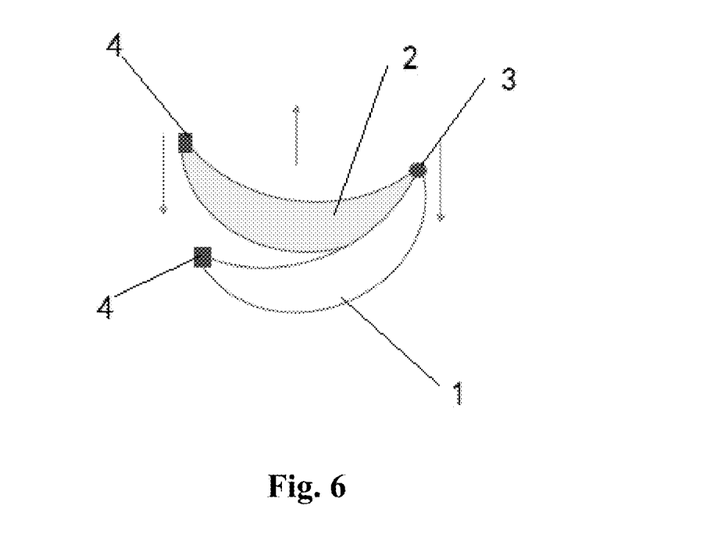
FIG. 6 shows a schematic view of a status after a first part rotates according to some embodiments of the present disclosure.

As shown in FIG. 3, the second end of the first part 1 and the second end of the second part 2 can be separated by a certain external force, and then the second part 2 is turned over around the connector 3, where the arrow in FIG. 3 indicates a turnover direction of the second part 2. As shown in FIG. 6, the second part 2 is turned over to have an identical bending direction to that of the semi-arc structure of the first part 1, then the first part 1 with the physiological status information collection unit is inserted in the hair; here, the hair needs to be clipped between the first part 1 and the second part 2, so a downward force is applied on the second end of the second part 2 to move the second end of the second part gradually close to the second end of the first part 1 and the hair is clipped by the first part 1 and the second part 2. A direction of the applied force is shown by a downward arrow in FIG. 6.

In the case that the wearable frame is to be switched from the hair clip shape to the wristband shape, an upward force is applied on the second end of the second part 2 to move the second end of the second part gradually away from the second end of the first part 1, where a direction of the applied force is shown by an upward arrow in FIG. 6. Then, the second part 2 is turned over to having a bending direction opposite to that of the semi-arc structure of the first part 1, and the second end of the first part 1 and the second end of the second part 2 are attached to each other through magnets 4, thereby presenting the wearable frame in the wristband shape.

In some embodiments of the present disclosure, the connector 3 is an elastic structure having a third status and a fourth status. The first part 1 or the second part 2 is provided with an accommodating space; in the case that the connector 3 is in the third status, the connector 3 is retracted inside the accommodating space, so that the first part 1 is tightly contacted with the second part 2; in the case that the connector 3 is in the fourth status, the connector 3 is in a stretching status to generate a gap between the first part 1 and the second part 2.

Figure 7:
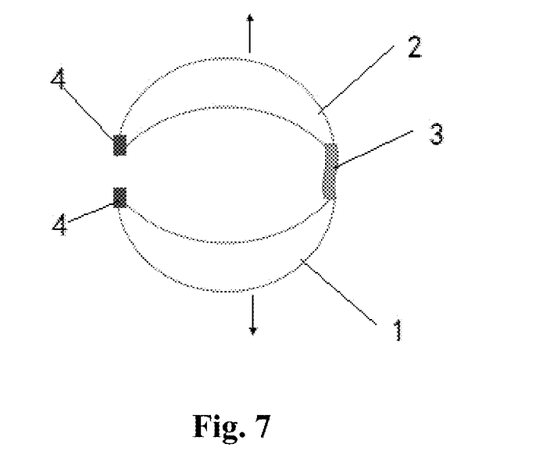
FIG. 7 shows a schematic view of a portable device changed from a wristband shape to a status that a first part is separated from a second part according to some embodiments of the present disclosure.
Figure 8:
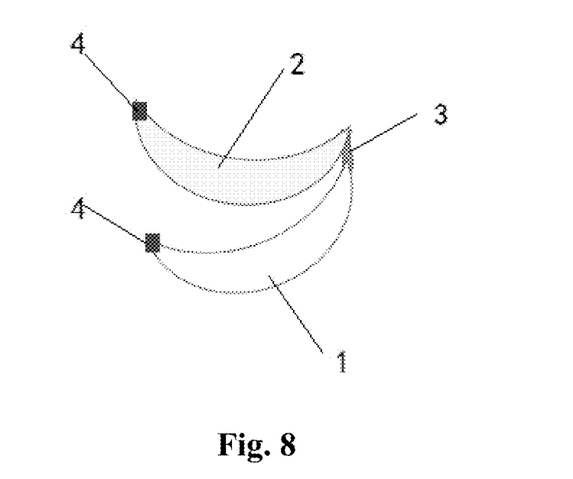
FIG. 8 shows a schematic view of a status that a first part is turned over to have an identical bending direction to that of a second part according to some embodiments of the present disclosure.
Figure 9:
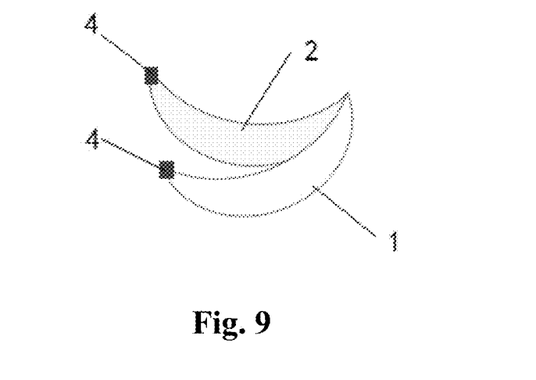
FIG. 9 shows a schematic view that an elastic structure is arranged in an accommodating space after a first part is turned over according to some embodiments of the present disclosure.
Figure 10:
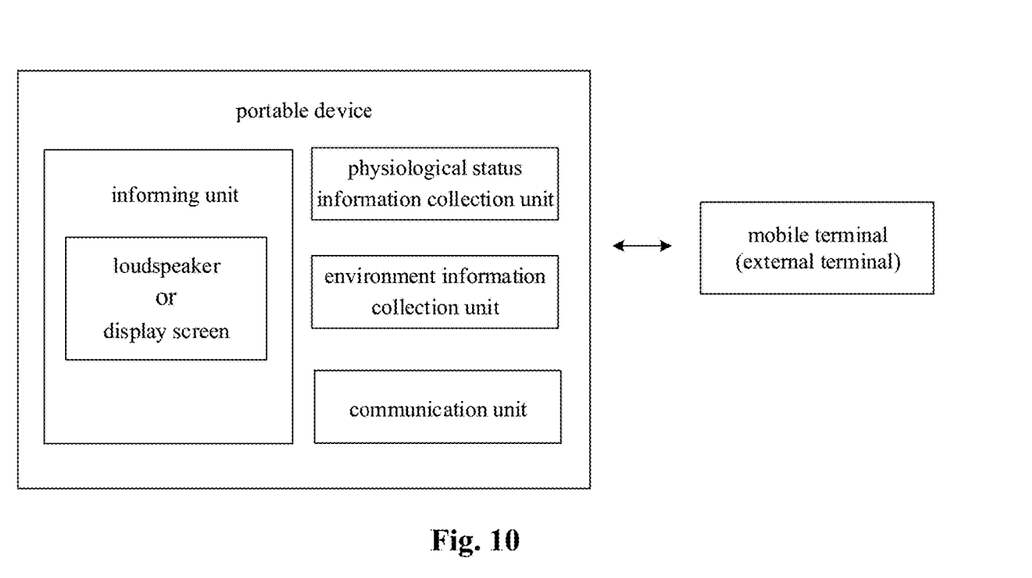
FIG. 10 shows a schematic view of a portable device assembly according to some embodiments of the present disclosure.

The elastic structure can be made of a flexible material, which can achieve a turnover action conveniently, and the flexible material may include rubber, plastic, etc. The elastic structure may include a counter-torque ruler having an identical principle and an identical structure to those of a flexible ruler that can automatically stretch out and retract). In general, the elastic structure is retracted inside the accommodating space. When switching from the wristband shape to the hair clip shape, the first part 1 and the second part 2 are pulled apart, as shown in FIG. 7; here, the elastic structure is in a stretching status, and actions like turnover can be conveniently achieved through the elastic structure. A status of the second part 2 after turnover is as shown in FIG. 8. After turnover, the elastic structure automatically retracts inside the semi-arc, as shown in FIG. 9. The wearable frame can be switched from the hair clip shape to the wristband shape through contrary actions as those described above.

Optionally, the wearable frame is made of a metal and has a relative small thickness.

Further, the wearable frame may be coated by a shell made of an electro-chromic material, which can have different colors under drive of an electric field, so as to be more nice-looking and practical.

It is also provided a portable device assembly in the present disclosure. The portable device assembly includes the portable device above, and further includes a mobile terminal. The communication unit of the portable device is used to send the physiological status information and the external environment information to the mobile terminal.

Further, the mobile terminal includes: an information processing unit, used to obtain a health suggestion suitable for the user according to information sent by the communication unit; and an informing unit, used to inform the user of the health suggestion.

Further, the informing unit includes: a loudspeaker, used to report the health suggestion to the user through a voice prompt, or a display screen, used to display the health suggestion to the user.

Further, the mobile terminal may be a mobile phone. Since the mobile phone is frequently used by the user, it is simple and convenient to operate the portable device assembly.

Through a mobile phone application (APP) which is installed in the mobile phone and corresponds to the portable device, the communication unit sends the physiological status information and the external environment information to the mobile phone, and the user can acquire the hair condition and skin condition through the mobile phone, and compare the physiological status information and the external environment information with data from a database in the APP, and can also acquire suggestions and analysis of experts or other users from the APP.

In the portable device assembly according to the embodiments of the present disclosure, the portable device can have a variety of forms including a ring shape, a hair clip shape, or the like. The portable device assembly can detect the entire external environment factors including ultraviolet, temperature, humidity and dust, and can also detect individual skin and hair status of each user, and can combine the external environment factors with the individual status of the user to give appropriate suggestions to the user.

Those described above are exemplary embodiments of the present disclosure. It should be noted that, the ordinary skilled in the art can make various improvements and modifications without departing from the principle of the disclosure, and those improvements and modifications all fall in the scope of protection of the present disclosure.

What is claimed is:

1. A portable device, comprising a wearable frame which is capable of switching at least between a first status and a second status, the wearable frame having different shapes in the first status and the second status;
  wherein the wearable frame is provided with:
    a physiological status information collection unit configured to collect physiological status information of a user;
    an environment information collection unit configured to collect external environment information about an environment where the user is located; and
    a communication unit configured to send the physiological status information and the external environment information to an external terminal;
  wherein the wearable frame comprises a first part and a second part, the physiological status information collection unit is arranged at the first part, the environment information collection unit is arranged at the second part, and the communication unit is arranged on the wearable frame;
  wherein the physiological status information collection unit is further configured to upload, through the communication unit, the physiological status information to the external terminal for analysis and storage,
  the environment information collection unit is further configured to upload, through the communication unit, the external environment information to the external terminal for analysis and storage, and
  the communication unit is further configured to receive a health information returned by the external terminal which is determined by analyzing the external environment information and the physiological status information by the external terminal.

2. The portable device according to claim 1, wherein in the first status, the wearable frame is in a ring shape, and in the second status, the wearable frame is in a clip shape.

3. The portable device according to claim 2, wherein the physiological status information collection unit comprises a bioelectric impedance analysis sensor; and
  the bioelectric impedance analysis sensor is configured to: obtain biological tissue status information of a skin of the user in the case that the wearable frame is in the first status; and obtain biological tissue status information of a hair of the user in the case that the wearable frame is in the second status.

4. The portable device according to claim 1, wherein the physiological status information collection unit comprises a first temperature sensor; and
  the first temperature sensor is configured to: obtain a temperature of a skin of the user in the case that the wearable frame is in the first status; and obtain a temperature of a hair of the user in the case that the wearable frame is in the second status.

5. The portable device according to claim 1, wherein the physiological status information collection unit comprises a potential of hydrogen sensor; and
  the potential of hydrogen sensor is configured to: obtain a potential of hydrogen value of a skin of the user in the case that the wearable frame is in the first status; and obtain a potential of hydrogen value of a hair of the user in the case that the wearable frame is in the second status.

6. The portable device according to claim 1, wherein the physiological status information collection unit comprises a camera having an enlarging function; and
  the camera is configured to: obtain information about a skin of the user in an enlarging status in the case that the wearable frame is in the first status; and obtain information about a hair of the user in an enlarging status in the case that the wearable frame is in the second status.

7. The portable device according to claim 1, wherein the environment information collection unit comprises at least one of the following: an ultraviolet sensor configured to detect an ultraviolet intensity, an air quality sensor configured to detect an air quality, a second temperature sensor configured to detect a temperature of an external environment, or a humidity sensor configured to detect a humidity of the external environment.

8. The portable device according to claim 1, wherein the first part and the second part are connected to each other through a connector, the first part is able to turn over around the connector to make the wearable frame change between the first status and the second status.

9. The portable device according to claim 8, wherein both the first part and the second part are in a semi-arc structure, a first end of the first part is connected to a first end of the second part through the connector, and a second end of the first part and a second end of the second part are magnetically attached to each other through magnets.

10. The portable device according to claim 8, wherein the connector comprises a first rotating bead and a second rotating bead that are connected to each other through a first shaft, the first rotating bead is connected to the first part through a second shaft, and the second rotating bead is connected to the second part through a third shaft.

11. The portable device according to claim 10, wherein the first rotating bead is sleeved on the first shaft and is able to rotate around the first shaft, the second shaft and the third shaft are parallel and are both perpendicular to the first shaft, the first rotating bead is sleeved on the second shaft, and the second rotating bead is sleeved on the third shaft.

12. The portable device according to claim 8, wherein the connector is an elastic structure having a third status and a fourth status, and the first part or the second part are provided with an accommodating space;
  wherein in the case that the connector is in the third status, the connector is retracted inside the accommodating space to make the first part closely contact with the second part; and
  in the case that the connector is in the fourth status, the connector is in a stretching status and there is a gap between the first part and the second part.

13. The portable device according to claim 1, wherein the wearable frame is coated by a shell made of an electro-chromic material, the electro-chromic material being able to display different colors when driven by an electric field.

14. The portable device according to claim 1, wherein the portable device further comprises:
  an informing unit which is arranged on the wearable frame and configured to inform the user of the health information returned by the external terminal.

15. The portable device according to claim 14, wherein the informing unit comprises:
  a loudspeaker configured to report the health information to the user through a voice prompt, or
  a display screen configured to display the health information to the user.

16. A portable device assembly, comprising a portable device, wherein the portable device comprises a wearable frame which is capable of switching at least between a first status and a second status, the wearable frame having different shapes in the first status and the second status;
  wherein the wearable frame is provided with:

a physiological status information collection unit configured to collect physiological status information of a user;

an environment information collection unit configured to collect external environment information about an environment where the user is located; and a communication unit, configured to send the physiological status information and the external environment information to an external terminal;

wherein the wearable frame comprises a first part and a second part, the physiological status information collection unit is arranged at the first part, the environment information collection unit is arranged at the second part, and the communication unit is arranged on the wearable frame;

wherein the physiological status information collection unit is further configured to upload, through the communication unit, the physiological status information to the external terminal for analysis and storage, the environment information collection unit is further configured to upload, through the communication unit, the external environment information to the external terminal for analysis and storage, and the communication unit is further configured to receive a health information returned by the external terminal which is determined by analyzing the external environment information and the physiological status information by the external terminal; and wherein the portable device assembly further comprises a mobile terminal, and the communication unit of the portable device is configured to send the physiological status information and the external environment information to the mobile terminal.

17. The portable device assembly according to claim 16, wherein the mobile terminal comprises:

an information processing unit configured to obtain a health information suitable for the user according to the information sent by the communication unit; and an informing unit configured to inform the health information to the user;

wherein the informing unit comprises:

a loudspeaker configured to report the health information to the user through a voice prompt, or a display screen configured to display the health information to the user.

* * * * *